US006610059B1

United States Patent
West, Jr.

(10) Patent No.: US 6,610,059 B1
(45) Date of Patent: Aug. 26, 2003

(54) ENDOSCOPIC INSTRUMENTS AND METHODS FOR IMPROVED BUBBLE ASPIRATION AT A SURGICAL SITE

(75) Inventor: Hugh S. West, Jr., Salt Lake City, UT (US)

(73) Assignee: HS West Investments LLC, Salt Lake City, UT (US)

( * ) Notice: Subject to any disclaimer, the term of this patent is extended or adjusted under 35 U.S.C. 154(b) by 0 days.

(21) Appl. No.: 10/083,750

(22) Filed: Feb. 25, 2002

(51) Int. Cl.[7] ............................................. A61B 18/18
(52) U.S. Cl. ........................................ 606/41; 606/46
(58) Field of Search ............................ 606/34, 41, 45, 606/46, 48–150, 170, 179, 180; 604/22

(56) References Cited

U.S. PATENT DOCUMENTS

| | | |
|---|---|---|
| 3,828,780 A | 8/1974 | Morrison, Jr. |
| 3,945,375 A | 3/1976 | Banko |
| 4,061,146 A | 12/1977 | Baehr et al. |
| 4,678,459 A | 7/1987 | Onik et al. |
| 4,815,462 A | 3/1989 | Clark |
| 4,850,354 A | 7/1989 | McGurk-Burleson et al. |
| 4,998,933 A | 3/1991 | Eggers et al. |
| 5,178,620 A | 1/1993 | Eggers et al. |
| 5,364,395 A * | 11/1994 | West, Jr. ................... 606/46 |
| 5,366,443 A | 11/1994 | Eggers et al. |
| 5,419,767 A | 5/1995 | Eggers et al. |
| 5,472,441 A | 12/1995 | Edwards et al. |
| 5,527,331 A * | 6/1996 | Kresch et al. ............. 606/170 |
| 5,540,708 A | 7/1996 | Lim et al. |
| 5,575,810 A | 11/1996 | Swanson et al. |
| 5,792,167 A | 8/1998 | Kablik et al. |
| 5,871,492 A * | 2/1999 | Sorensen ................... 606/166 |
| 5,904,681 A * | 5/1999 | West, Jr. ................... 606/41 |
| 5,961,532 A | 10/1999 | Finley et al. |
| 6,423,078 B1 * | 7/2002 | Bays et al. ................. 606/131 |
| 6,451,017 B1 * | 9/2002 | Moutafis et al. ............ 606/41 |

OTHER PUBLICATIONS

"*ArthroCare System 2000*", Reference Guide.
"*Arthro Wands®*", www.arthrocare.com, Product Information (Apr. 9, 2002).
"*Multi– and Single Electrode Electrosurgery for Patial Meniscectomy: Comparison of Depth of Injury and Ablation Rate*", Research Outcomes in Arthroscopic Surgery, ArthroCare Corporation, vol. 1, No. 1, Jun. 1995.
"*One System*", ArthroCare System 2000 for Arthroscopic Surgery, ArthroCare Corporation (Dec. 2000).
"*Use of Coblation Articular Cartilage Surgery*", Research Outcomes in Arthroscopic Surgery, vol. 3, No. 1, Mar. 1998.
"*Thermal Arthroscopy, Mitek VAPR System*", www.vapr.com/pages/whatsnew.html, Product Information (Apr. 8, 2002).
"*Vulcan EAS Ablator–S 2mm*", Oratec, Product Information (2002).

* cited by examiner

Primary Examiner—Michael Peffley
Assistant Examiner—Peter J Vrettakos
(74) Attorney, Agent, or Firm—Workman Nydegger

(57) ABSTRACT

Surgical apparatus and methods provide enhanced aspiration of gaseous bubbles and reduced drag during placement of the surgical apparatus. The surgical apparatus includes a rotatable cutting or shaving tool disposed within a hollow probe, an electrosurgical device on a side of the probe, and one or more aspiration holes or passages through a side of the probe in addition to a main opening at a distal end through which the cutting or abrading tool emerges. The aspiration holes are advantageously located adjacent to the lead electrode(s) of the electrosurgical device. Gaseous bubbles are preferentially aspirated through the aspiration holes. The aspiration holes also serve to reduce drag between the distal end of the surgical probe and soft tissue at, or adjacent to, the surgical site.

20 Claims, 8 Drawing Sheets

ENDOSCOPIC INSTRUMENTS AND METHODS FOR IMPROVED BUBBLE ASPIRATION AT A SURGICAL SITE

BACKGROUND OF THE INVENTION

1. The Field of the Invention

The invention is in the field of endoscopic instruments and methods for performing endoscopy. More particularly, the invention involves endoscopic instruments that perform the combined functions of mechanical cutting, electrosurgical cautery and/or ablation, and improved aspiration of gaseous bubbles.

2. The Relevant Technology

Endoscopy, a subset of which is arthroscopy, is gaining more and more favor as a less invasive means of diagnosing and surgically treating a wide variety of internal injuries or ailments. Endoscopic surgery is much less invasive than completely opening up the tissue and using conventional cutting tools. The result is greatly shortened patient recovery times, minimal scarring, reduced cost, and elimination of typical pre-operative and post-operative hospital stays.

The endoscope allows a doctor to look directly into a surgical site through a small incision, which allows for minimally invasive diagnosis and observation. Endoscopes include a magnifying lens and coated glass fibers that beam an intense, cool light into the surgical site. The surgical field is viewed on a video monitor that is electronically connected to an endoscopic video camera at the tip of the endoscope.

While viewing the surgical site in the manner described, the surgeon can perform any necessary repair and reconstruction using a separate surgical instrument inserted through a second small incision at the surgical site. The surgical instrument may include a mechanical cutting tool, such as a rotating blade or burr. Such mechanical cutting tools, or shavers, are well-known in the art and require no further explanation. In general, rotating blades are generally used to excise unwanted or damaged soft tissues, while rotating burrs are used to remove harder tissues, such as bone.

In addition to mechanical cutting or grinding tools, electronically powered cutting, cauterizing and ablating electrosurgical tools also allow for less invasive surgical procedures. Electrosurgical devices generally operate by imparting electromagnetic energy at a surgical site. Depending on the frequency of the energy delivered by the lead electrode, such devices can cauterize (i.e., heat seal) blood vessels, cut soft tissues, or ablate (i.e., vaporize) soft tissues. Electrosurgical devices are categorized as either "monopolar" or "bipolar" depending on the location of the negative, or return, electrode.

In a "monopolar" device, the return electrode is connected to the patient at a remote location relative to the lead electrode of the surgical device. In this manner, the electrical current generated by application of a voltage potential to the lead electrode passes from the lead electrode through the tissue or blood vessel being cut or cauterized, through the intervening tissue of the patient's body, and to a grounding pad located remotely on a patient's body. A substantial portion of the pathway through which the current passes is therefore the intervening tissue of the patient's body.

In contrast, the return electrode in a "bipolar" device is located in the near vicinity of one or more lead electrodes and attached to the same surgical instrument. Examples of multiple-lead bipolar devices are set forth in U.S. Pat. No. 4,988,933, U.S. Pat. No. 5,178,620, U.S. Pat. No. 5,366,443 and U.S. Pat. No. 5,419,767, all to Eggers et al. In general, bipolar devices work by passing varying levels of high frequency electrical energy through individually powered multiple leads and into the tissue to be ablated or cauterized. The current returns to the return, or common, electrode located on the same surgical instrument and connected to a ground by means of an insulated ground wire.

In general, both monopolar and bipolar devices can be used to cauterize, cut or ablate tissue depending on the power of the electromagnetic energy that is produced. When ablating tissues, gaseous bubbles comprising mostly water vapor are formed as a byproduct of ablation. Gaseous bubbles can be problematic because they can obscure the field of vision of the surgeon. In addition, gaseous bubbles can inhibit ablation by displacing the fluid needed to transmit electrical energy. Accordingly, some form of aspiration is typically required to continuously remove the gaseous bubbles from the surgical site.

One way is to provide a separate suctioning (or aspirating) device near the electrosurgical device. However, the use of two separate devices can be unwieldy and cumbersome, and it requires separate incisions for both devices. Moreover, the aspiration hole at the end of the aspiration tube must be kept away from surrounding tissue so as to avoid suctioning onto the tissue, which can plug the opening and prevent aspiration. Larger pieces of detached tissue, such as those that may be removed by mechanical means, can easily plug the aspiration tube, requiring removal and unplugging of the aspiration tube.

A better solution involves surgical instruments that combine a mechanical cutting or abrading tool with an electrosurgical device capable of ablation, together with an integral aspiration device. Surgical instruments combing a rotatable mechanical cutting or abrading tool, an electrosurgical instrument, and an integral aspiration device are disclosed in U.S. Pat. No. 5,364,395 to West, Jr. ("West I") and U.S. Pat. No. 5,904,681 to West, Jr. ("West II"). The West I and II patents describe surgical devices that include a hollow probe, a rotatable cutting or grinding tool disposed at least partially through an opening at the distal end or tip of the hollow probe, and an electrosurgical device comprising at least one electrode disposed on a side of the hollow probe at the distal end. The electrosurgical device may be either monopolar or bipolar as desired. Typically, mechanical cutting or grinding occurs on one side of the probe tip, and ablation, etc. occurs on the other side of the tip. In some embodiments, the cutting tool is hollow and provides a single hole at the end and an internal pathway through which debris and gaseous bubbles can be aspirated.

One advantage of the devices disclosed in the West I and II patents is the ability of the rotatable cutting or abrading tool to break apart or cut pieces of tissue that could otherwise plug or clog the hole. A downside of such surgical instruments is that they only include a single opening at the distal end of the probe for aspiration. This design often results in drag whenever the single opening at the distal end of the surgical device comes in contact with tissue adjacent or opposite to the tissue targeted for ablation, which causes the opening to suction onto or against the tissue. Such drag can inhibit the ability of the surgeon to properly position the distal end of the surgical device before ablation. It can further inhibit the ability to reposition the device during ablation. Such drag therefore hinders effective and accurate movement of the electrosurgical device whenever it is desired to use the electrosurgical device while the cutting or abrading tool is turned off.

An additional problem with the devices disclosed in the West I and II patents is the fact that the opening at the end of the probe is typically on a side of the probe opposite to the side of the electrosurgical device. As a result, the gaseous bubbles must travel around the sides and/or end of the probe in order to enter the opening within the probe. Depending on the location of the endoscope, gaseous bubbles traveling from one side of the probe to the other can continuously obscure the field of view during ablation, thus requiring periodic stoppages of the ablation process in order to allow for the removal of the gaseous bubbles and restore the field of view. The buildup of bubble may also interfere with tissue ablation by displacing the surrounding fluid. In order to effectively remove the bubbles, it may be necessary to reposition the surgical device, causing further inconvenience.

In view of the foregoing, it is readily apparent that improved aspiration means for aspirating gaseous bubbles from the surgical site are needed in order to reduce or eliminate drag between the surgical instrument and surrounding tissue and also in order to more efficiently remove gaseous bubbles from the field of view.

Such surgical instruments and methods for improved bubble aspiration at a surgical site are disclosed and claimed herein.

SUMMARY OF THE INVENTION

The present invention encompasses apparatus that combine a mechanical cutting or abrading tool, an electrosurgical device, and a suctioning device. Such apparatus provide for improved aspiration of gaseous bubbles and a reduction of drag during placement and/or repositioning of the surgical apparatus. The invention also encompasses improved methods for removing gaseous bubbles as they are generated in order to maintain an open field of view and also to reduce the accumulation of gaseous bubbles that can inhibit the operation of the electrosurgical device.

The improved aspiration of gaseous bubbles is accomplished by providing one or more aspiration holes near or in close proximity to the electrosurgical device. Because gaseous bubbles have negligible viscosity compared to the aqueous environment in which typical endoscopic procedures are performed, such gaseous bubbles are preferentially and efficiently aspirated and removed through the one or more aspiration holes. The one or more aspiration holes also serve to prevent or reduce drag, which can otherwise occur if the main opening of the surgical device probe touches and suctions onto soft tissues when positioning the surgical device with the mechanical cutting or abrading tool turned off.

In general, the surgical devices according to the invention include a hollow probe with a proximal end attached to a handle and a distal end where a mechanical cutting tool and an electrosurgical device are located. The hollow probe includes a hollow tubular member within which a drive shaft connected to the mechanical cutting or grinding tool is disposed. The cutting or grinding tool (e.g., a rotatable blade or burr) is preferably disposed at least partially within a main opening at the end of the hollow tubular member of the probe. The main opening of the tubular member may be slanted so as to enclose or shield one side of the rotatable cutting or abrading device while being open at the other side so as to leave a portion of the rotatable tool unshielded.

The electrosurgical device is advantageously attached to a surface of the hollow tubular member at or near the distal end of the probe. In the case where the main opening is slanted, the electrosurgical device will be disposed on or near that portion of the hollow tubular member that encloses a portion of the cutting or grinding tool. In this embodiment, one side of the distal end of the probe provides mechanical cutting or abrading and the other side provides electrosurgical capabilities.

The hollow tubular member of the probe not only encloses the drive shaft and, optionally, a portion of the cutting or abrading tool, it also provides a pathway through which fluid, solid debris, and gaseous bubbles can be continuously and/or intermittently be aspirated during the surgical procedure. In some cases, the drive shaft itself may be hollow so as to provide at least a portion of the actual aspiration pathway. In other cases, there may be a space between the drive shaft and the inner wall of the tubular member that provides the main aspiration pathway. Either way, the tubular member generally encloses the aspiration pathway.

Examples of surgical devices that combine mechanical cutting or abrading, an electrosurgical device, and aspiration capabilities are disclosed in U.S. Pat. No. 5,364,395 to West, Jr. and U.S. Pat. No. 5,904,681 to West, Jr. For purposes of disclosing apparatus that combine mechanical cutting or abrading, an electrosurgical device, and aspiration capabilities, the foregoing patents are incorporated herein by reference. As noted previously, one of the problems associated with the devices disclosed in the West I and II patents is that they only include a single opening through which fluids, debris and gaseous bubbles are aspirated. During mechanical cutting or abrading, the large opening associated with the mechanical cutting or shaving tool adequately aspirates and removes solid debris consisting of hard or soft tissue from the surgical site. When the cutting or abrading tool is in operation, the surgical device continuously aspirates pieces of hard and soft tissue as they are removed, together with ambient saline fluid. Tissues are typically aspirated through the main opening of the hollow probe. Larger pieces of solid debris are effectively chopped up and reduced in size by the rotating blade. However, when the mechanical blade or burr is stationary, such as when a surgical device is being initially positioned or when it is desired to only operate the electrosurgical device, continuous aspiration through the single hole at the end of the hollow probe can cause the distal end of the probe to suctionally adhere to soft tissue, thereby causing drag or resistance that can hinder ease of placement and repositioning of the surgical device.

Another problem is the relative inefficiency with which the single opening aspirates gaseous bubbles that may be generated by the electrosurgical device, such as when it is used to ablate soft tissues. During ablation, significant amounts of localized heat is generated, which causes water within the saline environment to evaporate to form gaseous bubbles. Such bubbles can quickly obscure the field of view otherwise provided by the endoscopic camera at the end of the endoscope. In addition, such gaseous bubbles can inhibit ablation by displacing the surrounding fluid used to generate an electrical currect in the vicinity of the soft tissue targeted for ablation. The main opening is not optimally positioned relative to the electrode for aspirating gaseous bubbles produced by the electrode, particularly when it is slanted. In some cases, the opening may be completely closed, thereby inhibiting bubble aspiration regardless of the orientation of the opening.

The present invention solves both problems, namely excessive drag and/or inefficient aspiration of gaseous bubbles, by providing one or more aspiration holes or openings in a side of the tubular member comprising the hollow probe so as to provide at least one aspiration hole in addition to the main opening at the distal end of the hollow probe. The aspiration hole through the side of the hollow tubular member effectively breaks the vacuum that can otherwise form when the main opening at the distal end of the hollow probe brushes against soft tissue. In this way, drag or other problems associated with adhesion of the probe to soft tissue is effectively eliminated, or at least greatly reduced. In order for there to be excessive drag resistance associated with the inventive surgical apparatus, both the main opening and the one or more aspiration holes would have to be simultaneously plugged or blocked by soft tissue at the surgical site, which is much less likely to happen than when the device includes a single opening for aspiration.

The one or more aspiration holes are preferably located in the vicinity of the electrosurgical device (i.e., "adjacent" to the electrosurgical device). Locating the one or more aspiration holes adjacent to the electrosurgical electrode generating the gaseous bubbles greatly enhances the efficiency by which gaseous bubbles can be aspirated and effectively removed from the surgical site as they are being formed during, e.g., ablation. Due to the negligible viscosity of gaseous bubbles, they are preferentially aspirated through the one or more aspiration holes compared to the surrounding fluid. The result is a much clearer field of view of the surgical site and reduced displacement of surrounding fluid.

Another aspect of the invention are methods for more efficiently removing gaseous bubbles from a surgical site during, e.g., ablation by the electrosurgical device. By maintaining constant aspiration through the hollow probe, the gaseous bubbles generated by the electrosurgical device are quickly and effectively aspirated through the one or more aspiration holes adjacent to the electrode generating the gaseous bubbles in order to maintain a clear field of view and avoid fluid displacement in the vicinity of the soft tissue targeted for ablation. The ability to more effectively remove gaseous bubbles is possible whether or not the mechanical cutting or abrading tool is rotating.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

I. Introduction and Definitions

Figure 1:
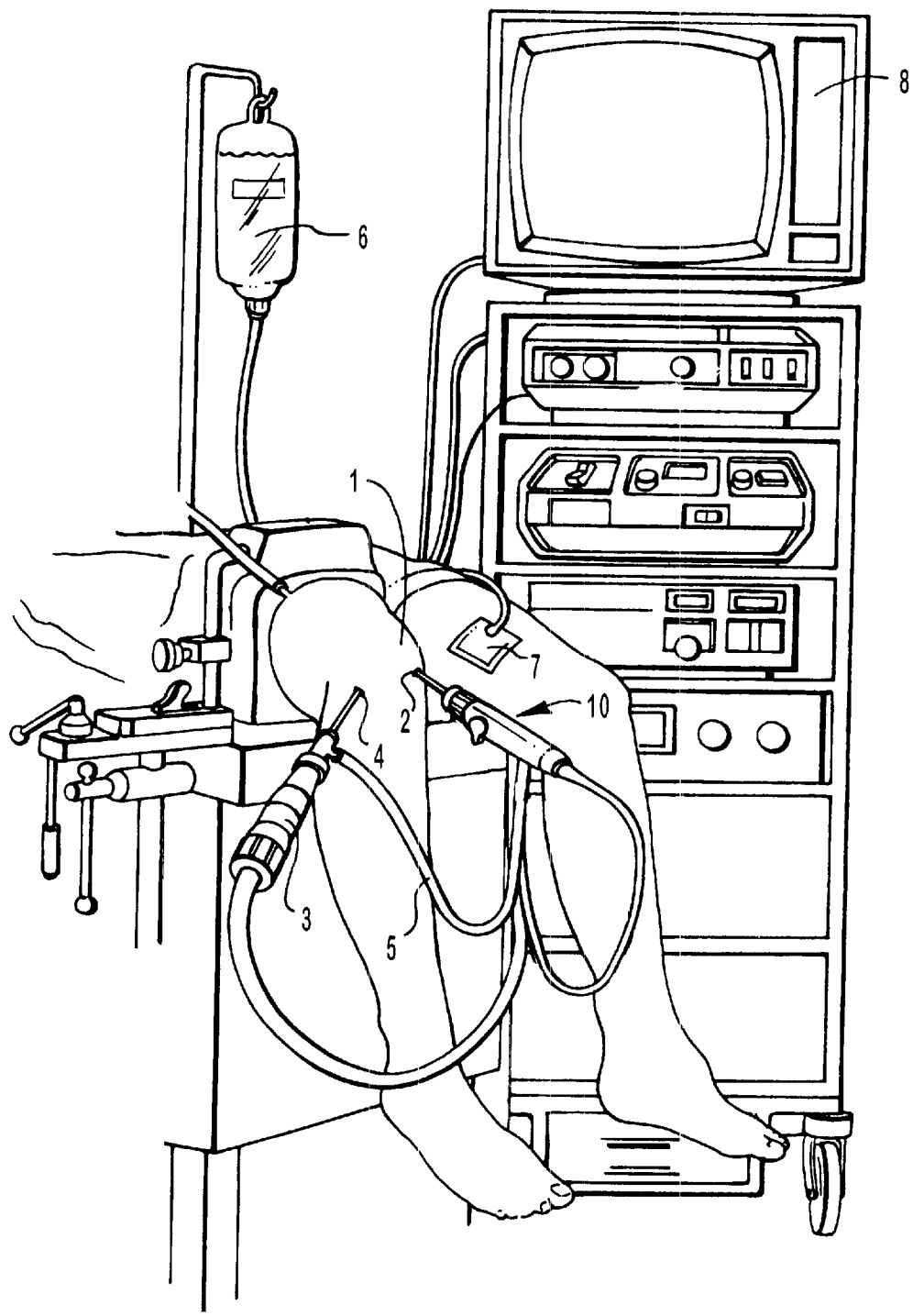
FIG. 1 is a perspective view of an operating room where an endoscopic surgical procedure is being conducted on the knee of a patient.

The present invention encompasses surgical instruments that allow for a variety of different surgical operations or functions to be performed using a single surgical instrument. The surgical instrument includes both a mechanical cutting tool, such as a serrated blade or a rotating burr, and an electrosurgical device that operates in either bipolar or monopolar mode in order to ablate, cauterize or cut soft tissues or blood vessels in or around the area where the mechanical cutting tool is used. In addition, the surgical instruments according to the invention include one or more aspiration holes, in addition to the main opening at a distal end of the surgical probe, that are advantageously adjacent to the electrosurgical device in order to efficiently aspirate gaseous bubbles that may occur as a result of, e.g., ablation.

The surgical instruments according to the invention can be used in any form of endoscopy. In the case of arthroscopic surgery in which bone or cartilage is removed, a preferred embodiment of the present invention will employ a rotatable burr for removing bone or cartilage in combination with an electrosurgical device for cutting or ablating soft tissues and/or for cauterizing blood vessels. It will readily be understood that other forms of endoscopy not involving bones or joints can also be performed using the surgical instruments of the invention. Where it is desired to remove soft tissues, the preferred mechanical cutting tool will include a rotatable blade rather than a burr.

The term "surgical site," as used in the description and appended claims, includes any location in the body of a patient where endoscopic surgery may be performed. Thus, although knees and other joints are common surgical sites for endoscopic surgery, the term "surgical site" as used in the description and appended claims, can include any location in the body of a patient where surgery may be performed.

The phrase "adjacent to the electrode," as used in the description and appended claims when referring to the location of the one or more aspiration holes relative to the one or more electrodes, shall be understood as encompassing any location that is sufficiently close to the electrode so as to facilitate aspiration of bubbles produced by the one or more electrodes. The phrase "adjacent to the electrode" shall not be limited to aspiration holes that are right next to the electrode but shall also include aspirating means that are located sufficient near the electrode so as to cause gaseous bubbles to be preferentially aspirated through the aspiration holes compared to the main opening. In general, the aspirating means will be located nearer the one or more electrodes than the main opening at the distal end of the hollow tubular member of the surgical instrument.

The terms "aspiration means" and "means for aspirating gaseous bubbles," as used in the description and appended claims, shall refer to one or more openings, holes, slots or other passages, in addition to the main opening, through the side of the hollow probe, through which gaseous bubbles can be aspirated. The term "aspiration means" also includes aspiration tubes or other structure separate from the hollow probe.

The term "side of the hollow member" includes all or substantially all of the structure between the proximal and distal ends.

The term "aspiration hole," as used in the specification and appended claims, refers to any discontinuity in the side of the hollow probe through which gaseous bubbles can be aspirated and/or which can serve to break the vacuum caused when the main opening brushes against soft tissues. The term "aspiration holes" broadly includes holes that are isolated from the main opening of a hollow probe (e.g., FIGS. 3–11) and those that are not isolated from the main opening (i.e., which have a channel, groove or other connection to the main opening) (e.g., FIGS. 12 and 13).

Terms such as "cautery" "ablation", "monopolar mode" and "bipolar mode" shall be afforded their ordinary and common meanings.

The terms "cutting tool" and "electrode," unless specifically limited, may include one or a plurality of individual cutting tools or electrodes, respectively.

In order to more specifically teach various embodiments of surgical devices according to the invention, reference will now be made to the drawings. The present invention is not limited to the particular embodiments depicted in the drawings, although such drawings represent preferred embodiments according to the invention.

FIG. 1 is a perspective view of an operating room where arthroscopic surgery is being conducted on the knee of a patient using a surgical instrument 10 according to the invention. In this case, the surgical instrument is adapted for arthroscopic surgery. A knee 1 is shown on an operating table with a surgical instrument 10 according to the invention inserted through a first incision 2 at the operating site. An endoscope 3 is inserted through a second incision 4 in the same general vicinity. An irrigation tube 5 attached to the endoscope 3 provides a continuous supply of sterile saline solution from a saline bag 6 in order to provide a clean and sterile saline environment at the surgical site. In the case where the surgical device 10 includes a monopolar surgical device, an optional grounding pad 7 may be attached to an appropriate location on the patient's body in order to complete the electrical circuit. The field of view of the surgical site is presented on a visual monitor 8.

Figure 2:
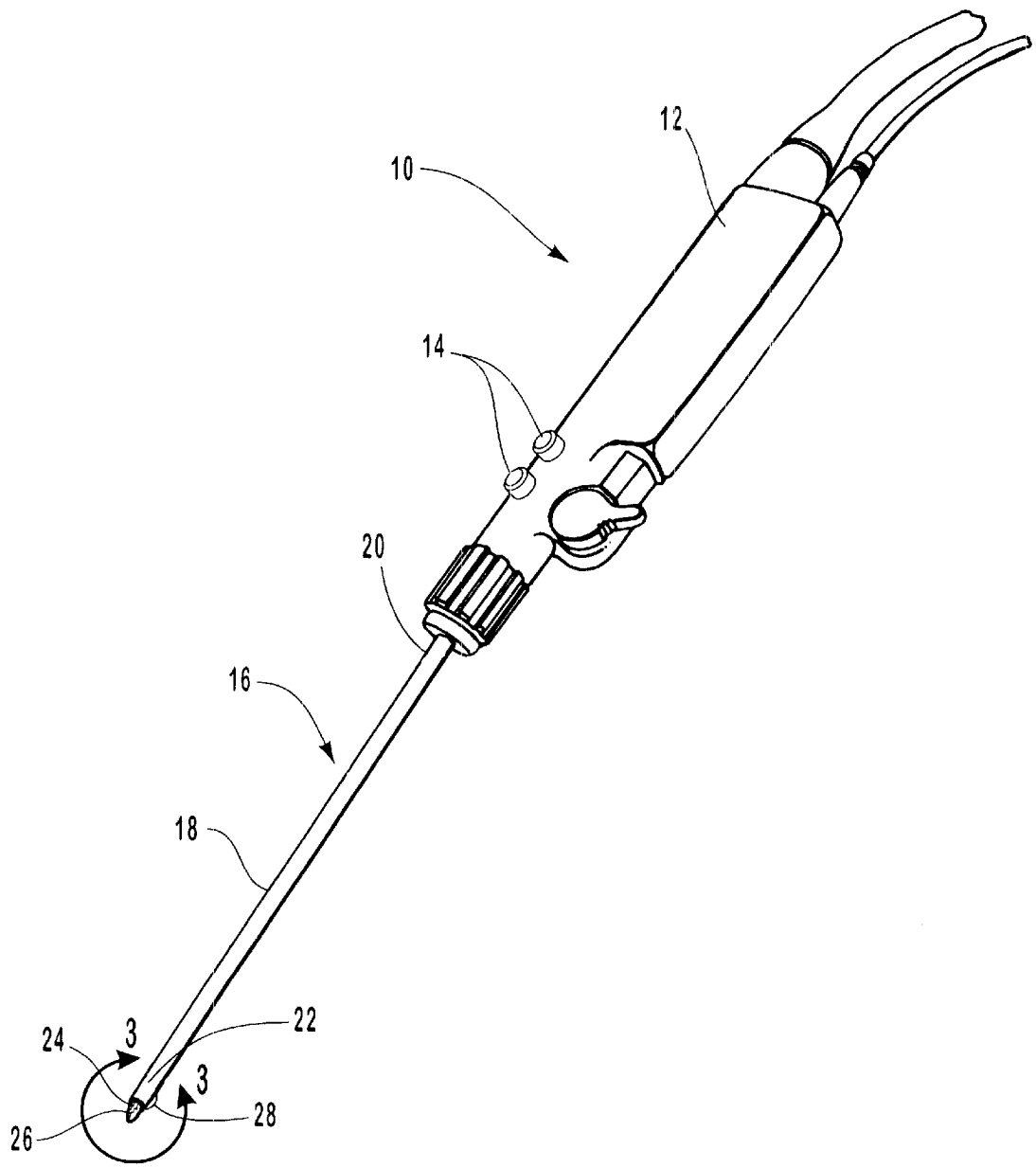
FIG. 2 is a perspective view of an endoscopic surgical device that combines a mechanical cutting or abrading tool, an electrosurgical device, and aspiration capabilities.

FIG. 2 depicts an exemplary surgical device 10 according to the invention that is provided with both a mechanical cutting or shaving tool, such as a rotatable blade or burr, an electrosurgical device for cauterizing blood vessels or removing hard and soft tissues, and aspiration means. The surgical instrument 10 advantageously includes a handle 12, which may include one or more control buttons 14 for carrying out a desired operation. One of ordinary skill in the art will be able to design an appropriate handle 12 having an appropriate number, size and orientation of control buttons 14 in order to facilitate and control the operation of the surgical device 10 as desired.

The surgical device 10 further includes a hollow probe 16 that further comprises a hollow tubular member 18 having a proximal end 20 attached to the handle 12 and a distal end 22 where the mechanical cutting tool and electrosurgical device are located. At the distal end 22 of the tubular member 18 is a main opening 24 through which a rotatable cutting or abrading tool 26 is at least partially disposed. The rotatable cutting or abrading tool is attached to a drive shaft (not shown) that causes the rotatable cutting or abrading tool to rotate at a desired speed during mechanical cutting or abrading. Also disposed at the distal end 22 of the hollow tubular member 18 is an electrosurgical device 28 that includes one or more electrodes.

The purpose of the rotating cutting or abrading tool is to remove hard or soft tissues from the surgical site. In general, abrading tools are better suited for removing harder tissues such as bone, while cutting or shaving tools are better suited for removing softer tissues, such as cancerous cells, surrounding healthy soft tissue, and cartilage. When the cutting or abrading tool is in operation, the surgical device continually aspirates pieces of hard or soft tissue as they are removed through the main opening 24 of the tubular member 18. Larger pieces of solid debris can be effectively chopped up or reduced in size by a rotating blade or other cutting tool.

The electrosurgical device 28 can be used to perform any surgical function carried out by electrosurgical devices, e.g., cutting, cautery, and/or ablation. The electrosurgical device 28 may be designed so as to operate in monopolar or bipolar mode, as desired. Although both monopolar and bipolar devices are often used to carry out the same function, monopolar electrosurgical devices are typically better suited for cautery and cutting, while bipolar devices are better suited for ablation. Nevertheless, it is within the scope of the invention to use electrosurgical device 28 for any desired function, whether operating in monopolar or bipolar mode. When used to ablate tissues, gaseous bubbles are often formed as the surrounding saline solution and/or bodily fluids are heated to above the boiling point of water. Some of the gaseous bubbles may be aspirated through the main opening 24.

Figure 3:
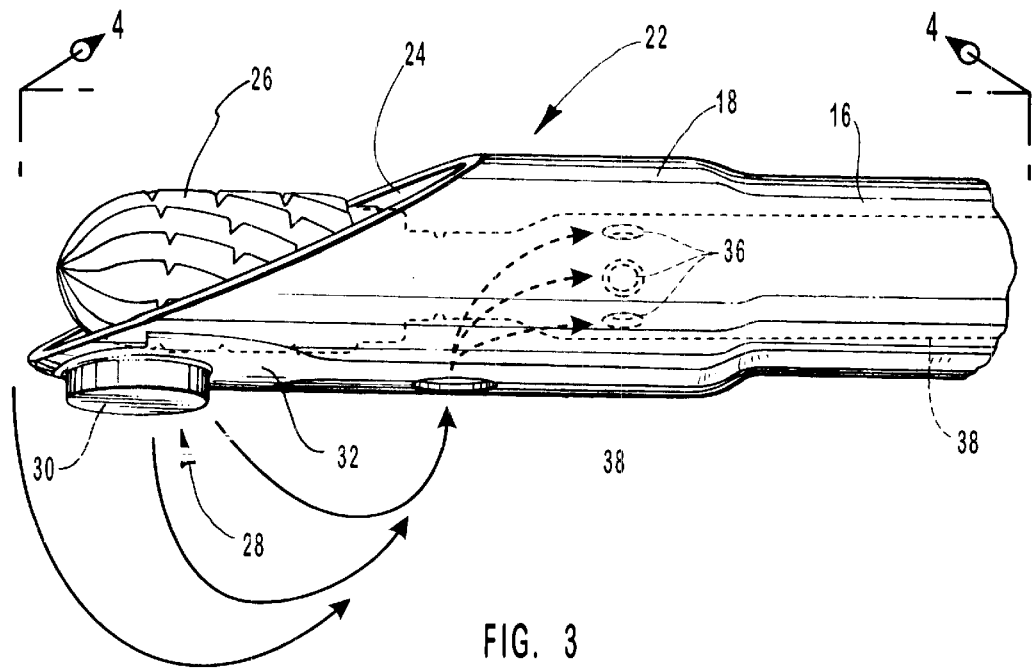
FIG. 3 is a perspective view of the distal end of an endosurgical device according to the invention incorporating a rotatable burr and an aspiration hole adjacent to a lead electrode of an electrosurgical device.
Figure 4:
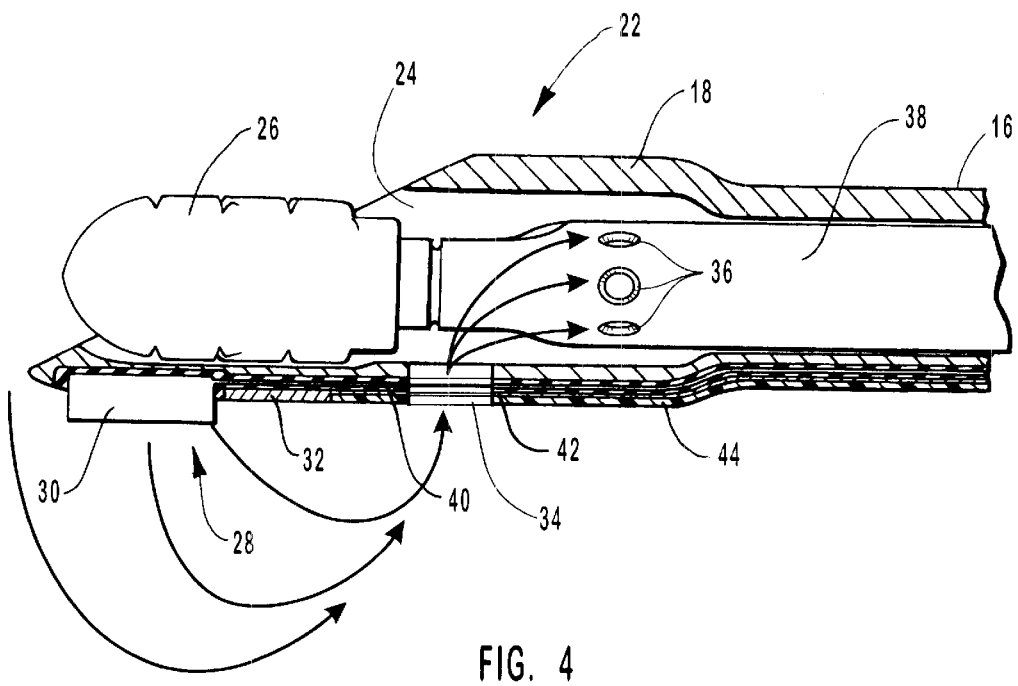
FIG. 4 is a cross-sectional view of the device depicted in FIG. 3 taken along cutting line 4—4.

FIGS. 3 and 4 depict apparatus and features assciated with one embodiment of the distal end 22 of the probe 16. These figures depict a rotable burr 26 disposed partially through the main opening 24 of the distal end 22 of the hollow tubular member 18. Because the tubular member 18 is hollow, it defines a central passageway. The rotatable burr 26 is attached to a hollow drive shaft 38 disposed within the central passageway of the hollow tubular member 18. The drive shaft 38 is advantageously hollow and includes one or more auxiliary holes 36 through which gaseous bubbles and/or solid debris may be aspirated. The main opening 24 at the distal end 22 of the hollow tubular member 18 is slanted so as to partially enclose the rotatable burr 26. In this way, only one side of the distal end 22 of the hollow tubular member 18 provides cutting or abrading, while the other side provides an attachment site for the electrosurgical device 28.

As also shown in FIGS. 3 and 4, the electrosurgical device 28 includes a single lead electrode 30 attached to a side of the hollow tubular member adjacent the rotatable burr 26. It will be appreciated, however, that the lead electrode 30 may be positioned at any suitable location on the hollow tubular member 18. In addition, multiple lead electrodes may be included. The lead electrode 30 is typically isolated electrically from the hollow tubular member 18 so that the lead electrode 30 provides the desired voltage potential rather than the hollow tubular member 18, e.g., in the event that the hollow tubular member 18 is made of metal. If the surgical device is to be used in monopolar mode, the lead electrode 30 will be the only electrode located along the hollow tubular member 18 (unless one or more additional lead electrodes are provided). No grounding electrodes will be located anywhere along the hollow tubular member 18. Instead, the grounding electrode will be attached to the patient's body at an alternative location (see FIG. 1, grounding pad 7).

In the event that the electrosurgical device 28 is intended for operation in bipolar mode, a grounding electrode will typically be provided and located near the one or more lead electrodes 30. As shown in FIGS. 3 and 4, a grounding electrode 32 may be integrally formed within the hollow tubular member 18 in a manner so as to be electronically isolated from the lead electrode 30. The grounding electrode 32 may or may not be electronically isolated relative to the remaining hollow tubular member 18. The lead electrode 30 is powered by a lead wire 40 that is advantageously embedded within the hollow tubular member 18. Similarly, the grounding electrode 32 is attached to a grounding wire 42. As shown in FIG. 4, each of the lead electrode 30, grounding electrode 32, lead wire 40, and grounding wire 42 are electronically isolated and protected by means of an insulating sheath 44. It will be appreciated, however, that one of ordinary skill in the art will be able to select an appropriate design that will cause the electrosurgical device 28 to function in a desired manner.

The hollow tubular member 18 also includes one or more aspiration holes 34 adjacent to the lead electrode 30. The purpose of the one or more aspiration holes 34 is to efficiently and effectively aspirate gaseous bubbles that may be generated by the electrosurgical device 28, such as when it is used to ablate tissues. The aspiration holes 34 comprise aspiration means for aspirating gaseous bubbles from the surgical site. The auxiliary holes 36 through the hollow drive shaft 38, together with the central passageway defined by the hollow tubular member 18, provide a continuous pathway for the aspiration of gaseous bubbles, as shown by the arrows depicted in FIGS. 3 and 4.

Figure 5:
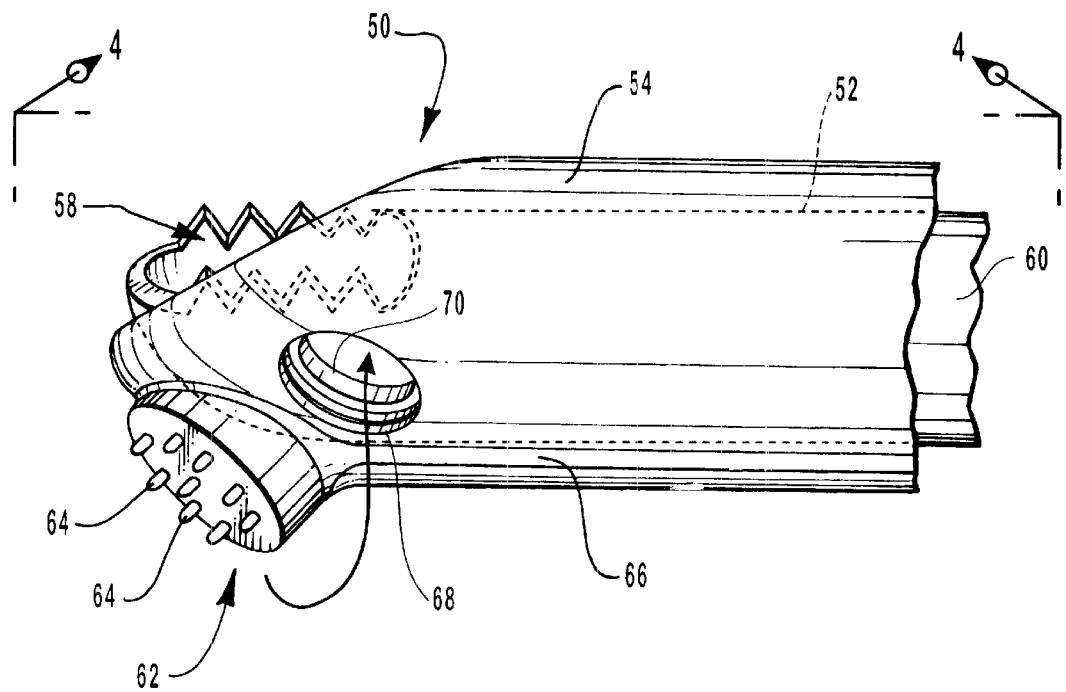
FIG. 5 is a perspective view of an alternative embodiment of a surgical device according to the invention that includes a rotatable blade and a pair of aspiration holes adjacent to multiple lead electrodes of an electrosurgical electrode.
Figure 6:
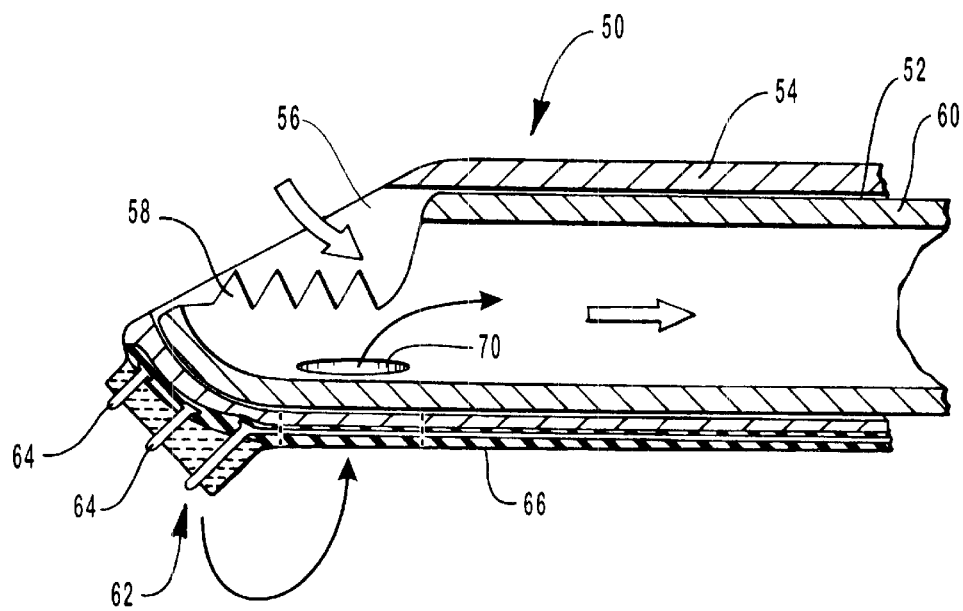
FIG. 6 is a cross-section view of the device depicted in FIG. 5 taken along cutting lines 6—6.
Figure 7:
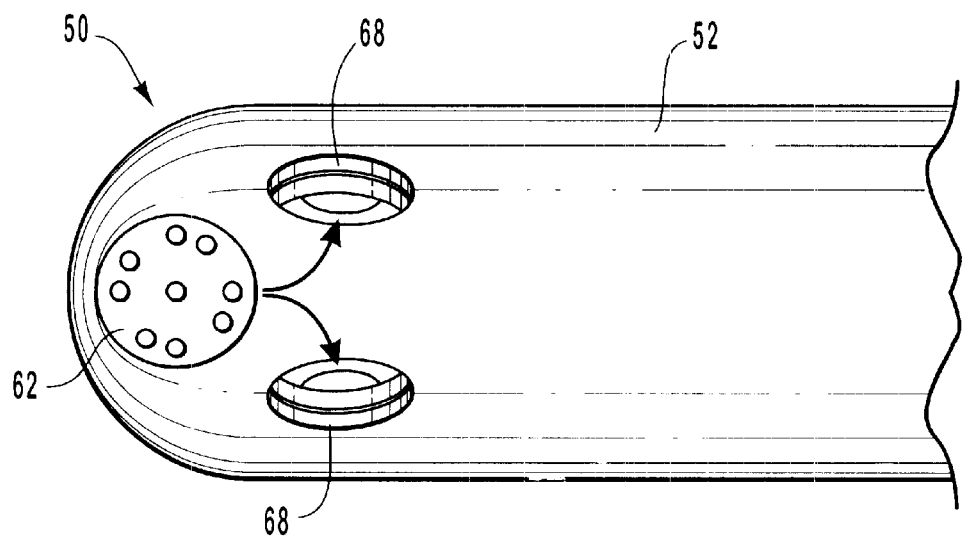
FIG. 7 is a side view of the surgical device depicted in FIGS. 5 and 6.

FIGS. 5–7 depict an alternative surgical device according to the present invention that includes a rotatable cutting or shaving tool instead of a rotatable burr. In addition, this embodiment illustrates an electrosurgical device that includes multiple lead electrodes. More particularly, a distal end 50 of a surgical probe or device 52 according to the invention includes a tubular member 54 having a main opening 56. A hollow shaver 58, as shown with serrated edges, is attached to a hollow drive shaft 60 disposed within a central passageway of the tubular member 54. Because the main opening 56 is slanted, the distal end 50 of the tubular member 54 partially encloses the hollow shaver 58 so that one side of the distal end 50 provides shaving and cutting while the other side does not. It will be appreciated that the shaver 58 need not have a serrated edge but may also include a smooth edge or an edge having any other desired shape. The hollow shaver 58 and hollow drive shaft 60 define a continuous aspiration pathway through which severed tissues and other debris can be effectively aspirated and removed from the surgical site. The aspiration pathway for the severed tissues and other debris illustrated by the larger arrows depicted in FIG. 6.

The distal end 50 of the surgical probe 52 also includes an electrosurgical device 62 having a multiplicity of lead electrodes 64. An insulating sheath 66 electronically isolates the lead electrode 64 from the tubular member 54 which, if made of metal, can serve as the ground or return electrode. It will be appreciated that any desired electrosurgical device may be used in combination with the rotatable cutting tool 58.

As better shown in FIGS. 5 and 7, the tubular member 54 further includes one or more aspiration holes 66 adjacent to the electrosurgical device 62. The purpose of the aspiration holes 68 is to provide an aspiration pathway through which gaseous bubbles produced by the electrosurgical device 62 can be effectively and efficiently aspirated. In this way, the gaseous bubbles produced by the electrosurgical device 62, e.g., as a result of ablation, can be quickly removed so as to maintain a clear field of view of the surgical site and also to reduce fluid displacement and avoid a buildup of electrical resistance in the vicinity of the electrosurgical device 62. The aspiration holes 66 comprise aspiration means for aspirating gaseous bubbles from the surgical site. The hollow drive shaft 60 may optionally include one or more auxiliary holes 70 in order to minimize the chance that a surface of the hollow drive shaft 60 opposite the shaver 58 will entirely obscure the one or more aspiration holes 68, as will be discussed more fully below when describing another embodiment.

Figure 8:
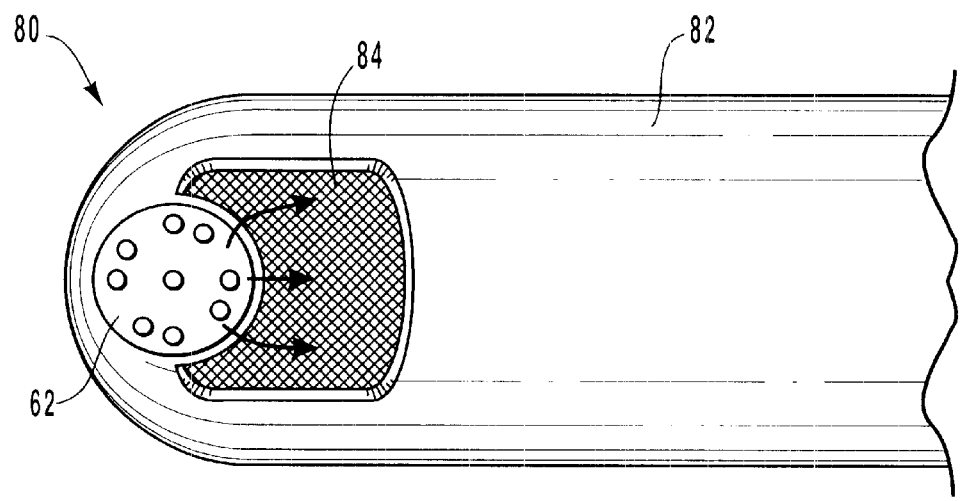
FIG. 8 is an alternative embodiment of the surgical instrument according to the invention that includes an aspiration mesh adjacent to the lead electrode of an electrosurgical device which mesh comprises a large number of aspiration holes.

FIG. 8 depicts an alternative embodiment that includes mesh aspiration means comprising a large number of tiny aspiration holes. More particularly, a distal end 80 of a surgical probe 82 according to the invention includes an electrosurgical device 62 and an aspiration mesh 84 adjacent thereto. The aspiration mesh 82 serves as aspiration means for aspirating gaseous bubbles from the surgical site.

Figure 9:
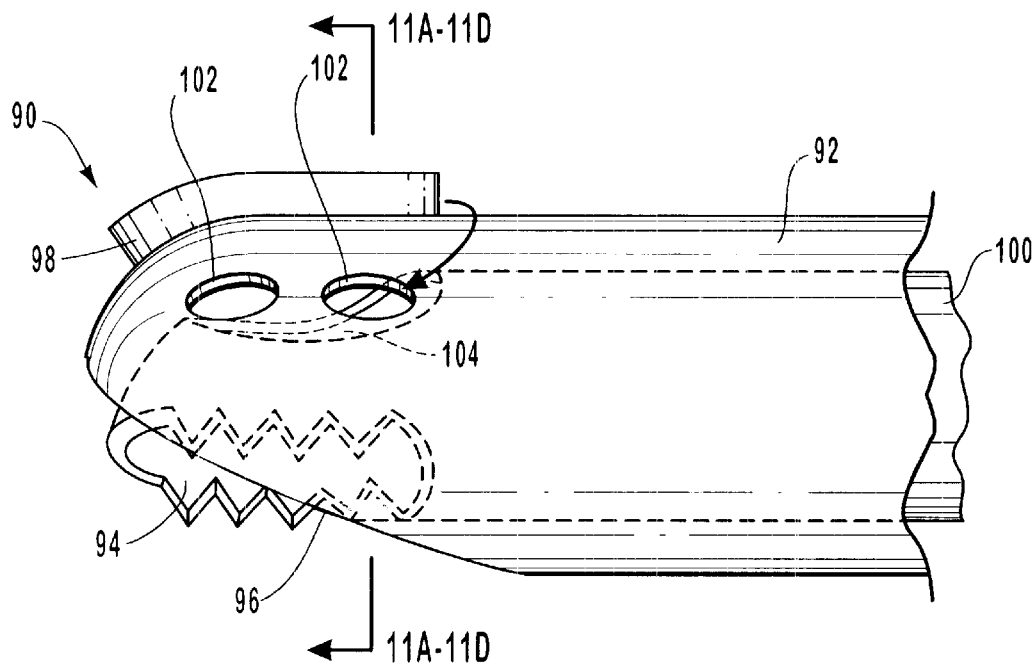
FIG. 9 is an alternative embodiment of a surgical device according to the invention that includes a rotatable blade and a pair of aspiration holes on either side of an elongate lead electrode of an electrosurgical device.
Figure 10:
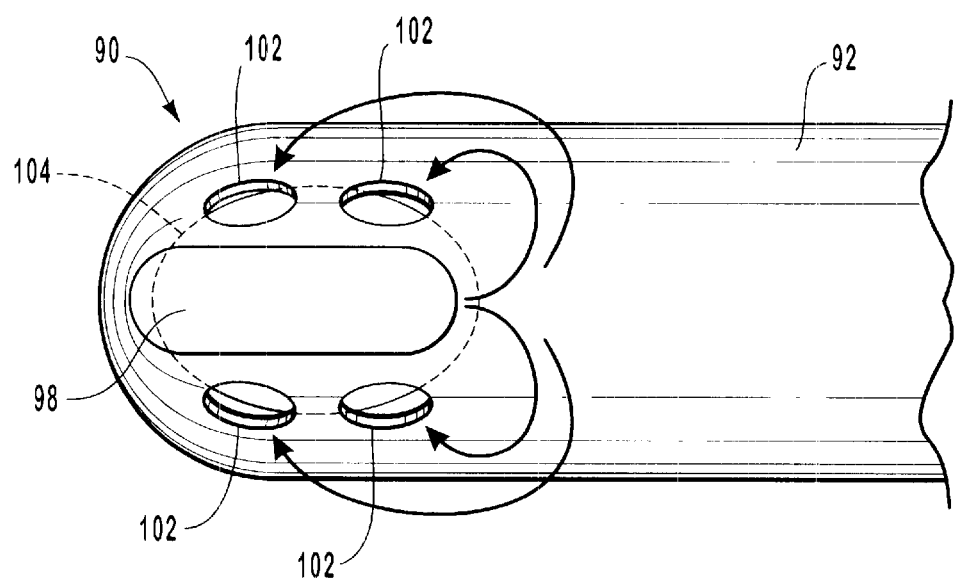
FIG. 10 is a side view of the device depicted in FIG. 9.

FIGS. 9–11 depict another embodiment of the invention that includes a pair of aspiration holes on either side of an elongate electrode. As more particularly depicted in FIGS. 9 and 10, a distal end 90 of a surgical probe 92 includes a rotatable cutting blade 94 that is partially disposed through, but protected by, a slanted main opening at the distal end 90 of the hollow probe 92. An elongate electrode 98 is disposed on a side of the probe opposite the rotatable blade 94. The rotatable blade 94 is connected to a hollow drive shaft 100. The combination of the hollow cutting blade 94 and the hollow drive shaft 100 provides a continuous aspiration pathway through the main opening 11 of a distal end 90 of the probe 92. This aspiration pathway is used to remove soft tissue and other debris from the surgical site, e.g., as a result of mechanical cutting or shaving.

On either side of the electrode 98 are a pair of aspiration holes 98 that provide an additional aspiration pathway for removing gaseous bubbles generated by the electrode 98. The hollow drive shaft 100 may optionally include auxiliary holes 104 that facilitate aspiration of gaseous bubbles through the aspiration holes 102. The interaction of the various components to provide an aspiration pathway that facilitates aspiration of gaseous bubbles is better depicted in FIGS. 11A–11D.

Figure 11A:
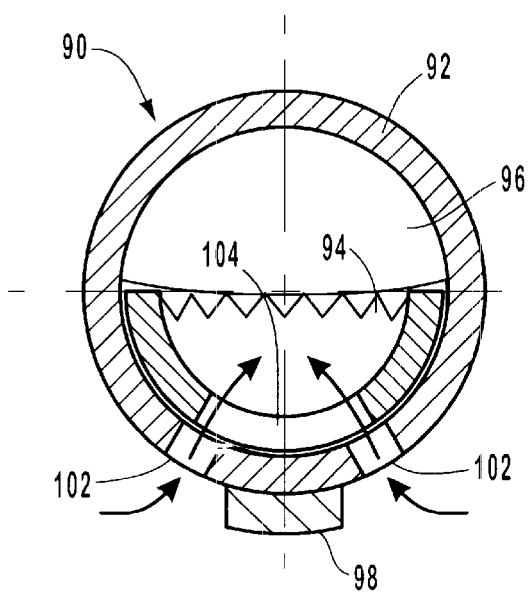
FIGS. 11A–11D depict various possible angular orientations of the cutting tool relative to the aspiration holes.
Figure 11B:
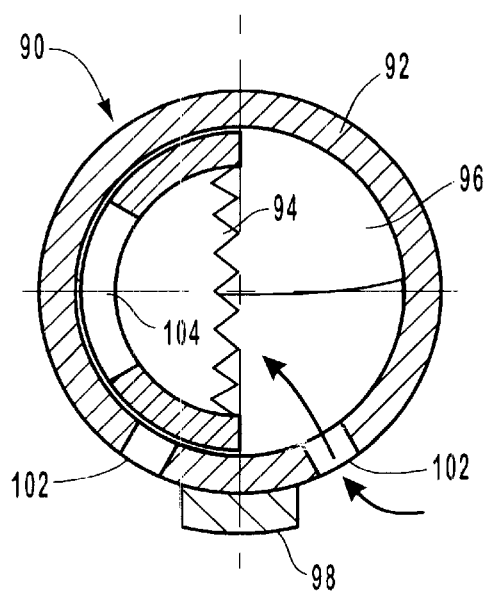
Figure 11C:
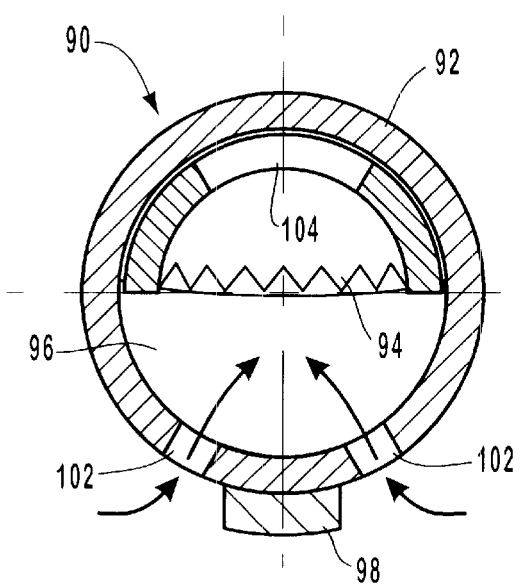
Figure 11D:
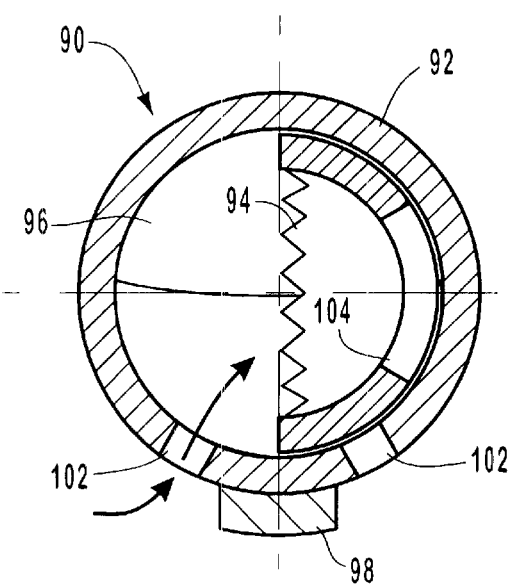

FIGS. 11A and 11D show how the position of the rotatable cutting blade 94 relative to the hollow drive shaft 100 can affect, whether or not one or both pairs of aspiration holes 102 are open and able to aspirate gaseous bubbles. FIG. 11A depicts the situation in which the aspiration holes 98 are entirely blocked by the backside of the rotatable cutting blade 94. However, an aspiration pathway for efficiently removes gaseous bubbles is still possible in the event that optional auxiliary holes 104 are included.

FIG. 11B depicts the rotatable cutting blade rotated 90° relative to the orientation of FIG. 11A. In this orientation, one of the sets of aspiration holes 102 is open while the other may be obscured or blocked (depending on the existance and position of auxiliary holes 104).

FIG. 11C depicts the situation where the rotatable cutting blade 94 is rotated 180° relative to the rotational orientation of FIG. 11A. In this situation, all four aspiration holes 102 are completely open and unobstructed. In this case, the optional auxiliary holes 104 are not needed.

Finally, FIG. 11D is the mirror-image of FIG. 11B in which one of the sets of aspiration holes 102 is open while the other is obscured or blocked (depending on the existance and position of auxiliary holes 104).

Whether the rotatable cutting blade 94 happens to stop in any of the orientations depicted in FIGS. 11A–11D, or one of the many other possible orientations, is a matter of random chance. In reality, even without optional auxiliary holes 104, there is a high probability that at least a portion of the aspiration holes 102 will be open at any given orientation of the rotatable cutting blade 94. The existence of the auxiliary holes 104 simply increases the probability that an aspiration pathway through aspiration holes 102 will be available for a given rotational orientation of the rotatable cutting blade 94.

Although not required, it is certainly within the scope of the invention to provide a microswitch or some other means for ensuring that the rotational cutting blade 94 stops at a rotational orientation that ensures that the aspiration holes 102 at least partially unblocked. If it is desired to ensure a particular angular orientation of the rotatable cutting blade 94, one of ordinary skill in the art will be able to readily design such a system using microswitches or any other electronic or mechanical devices known in the art.

Of course, the rotational orientation of the rotatable cutting blade 94 is subject to random chance, because in the event that the aspiration holes 102 are entirely blocked, the practitioner can simply toggle the rotatable cutting blade 94 briefly in order to reorient it so as to at least partially open the aspiration holes 102.

Figure 12A:
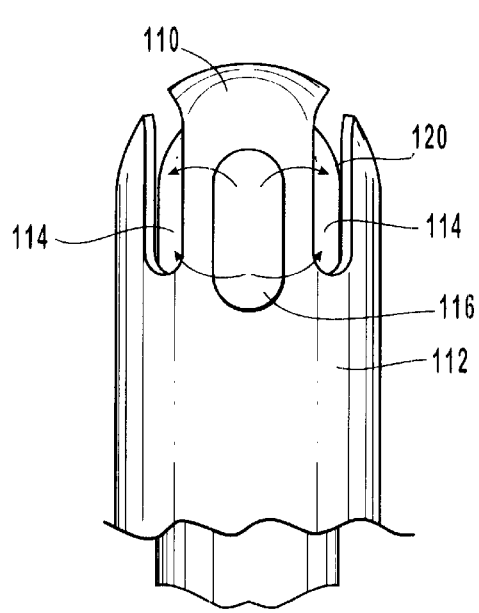
FIGS. 12A–12B depict an inventive surgical device in which the aspiration holes are separate but not isolated from, the main opening.
Figure 12B:
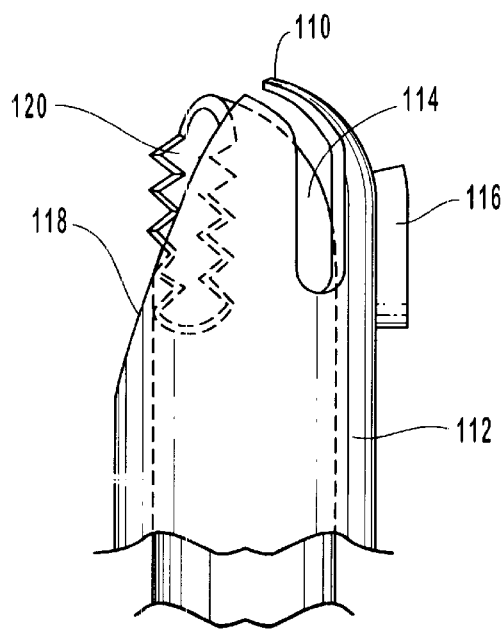

FIGS. 12A and 12B depict another embodiment of a surgical device according to the invention, particularly a distal end 110 of a surgical probe 112 that includes aspiration holes or slots 114 on either side of an electrode 116. The aspiration slots 114 are separate but not isolated from a main opening 118 through which a rotatable cutting tool 120 is disposed. The purpose of this embodiment is to illustrate that the aspiration holes need not be discontinuous or isolated relative to the main opening but, rather, can perform their function even if continuous with, or not isolated from, the main opening 18. The aspiration slots 114 are "separate from" the main opening 118 because they structurally extend an opening from the main opening to a location that is adjacent to the electrode 116. One purpose of the main opening 118 is to provide passage of the rotatable cutting tool 120 therethrough, while a purpose of the aspiration slots 114 is to provide aspiration of gaseous bubbles and/or to reduce or eliminate drag during placements or repositioning of the surgical probe 112.

Figure 13A:
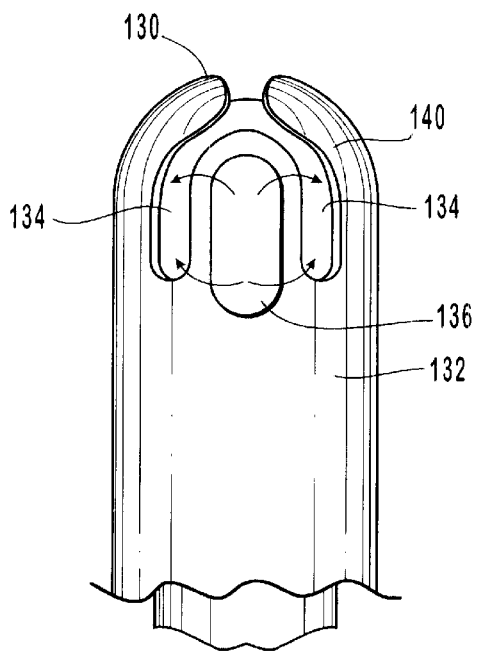
FIGS. 13A–13B also depict an inventive surgical device in which the aspiration holes are separate but not isolated from, the main opening.
Figure 13B:
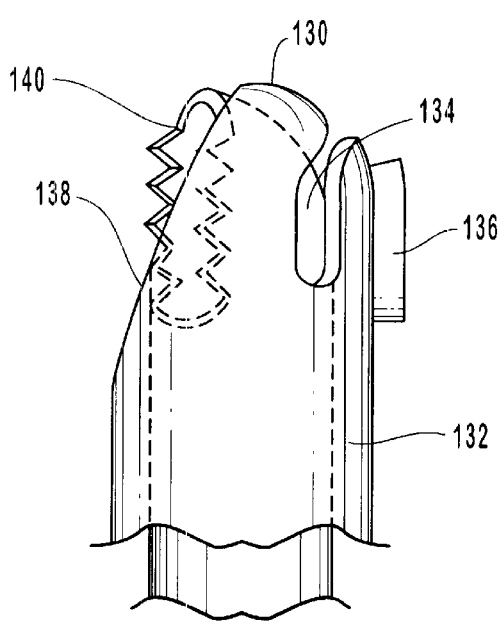

FIGS. 13A and 13B likewise depict a distal end 130 of a hollow surgical probe 132 that includes aspiration holes or slots 134 on either side of an electrode 136. The aspiration slots 134 are separate but not isolated from, a main opening 138 through which a cutting tool 140 is disposed. The aspiration slots 134 function similarly to the aspiration slots 114 depicted in FIGS. 12A and 12B. Aspiration holes or slots 114 and 134 comprise aspiration means separate from the main opening, for aspirating gaseous bubbles.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A surgical instrument used in endoscopic surgery, comprising:
    a hollow member having a central passageway and a main opening through a distal end thereof;
    a rotatable cutting tool disposed at the distal end of the hollow member;
    an electrode adapted for ablating tissue disposed at the distal end of the hollow member; and
    aspiration means, separate from the main opening and disposed in a side of the hollow member adjacent to the electrode, for aspirating gaseous bubbles generated when tissue is ablated by the electrode.

2. A surgical instrument as defined in claim 1, wherein the hollow member is in fluid communication with an aspirator.

3. A surgical instrument as defined in claim 2, wherein the main opening at the distal end of the hollow member provides aspiration of at least one of fluid, tissue and gaseous bubbles at a surgical site.

4. A surgical instrument as defined in claim 1, wherein the rotatable cutting tool is disposed at least partially within the main opening of the hollow member.

5. A surgical instrument as defined in claim 1, wherein rotatable cutting tool comprises at least one of a burr or a blade.

6. A surgical instrument as defined in claim 1, wherein the rotatable cutting tool comprises a hollow drive shaft.

7. A surgical instrument as defined in claim 6, wherein the hollow drive shaft further includes at least one auxiliary hole through which bubbles can be aspirated.

8. A surgical instrument as defined in claim 1, wherein the electrode comprises at least a portion of an electronic surgical device that operates in at least one of a monopolar mode or a bipolar mode.

9. A surgical instrument as defined in claim 8, wherein the electronic surgical device is adapted to selectively perform cautery in addition to ablation.

10. A surgical instrument as defined in claim 1, wherein the aspiration means comprises at least one aspiration hole through a side of the hollow member.

11. A surgical instrument as defined in claim 10, wherein the aspiration hole is disposed adjacent to the electrode.

12. A surgical instrument as defined in claim 10, wherein the surgical instrument includes at least one aspiration hole on one side of the electrode and at least one other aspiration hole on another side of the electrode.

13. A surgical instrument as defined in claim 10, wherein the at least one aspiration hole comprises a mesh structure adjacent to the electrode.

14. A surgical instrument as defined in claim 1, wherein the aspiration means includes at least one slot extending form an end of the hollow member adjacent the main opening to a location adjacent the electrode.

15. A surgical instrument as defined in claim 1, wherein the aspiration means comprises at least one aspiration tube separate from the hollow member.

16. A surgical instrument used in endoscopic surgery, comprising:
- a hollow tubular member having a main opening through a distal end thereof;
- a rotatable cutting blade disposed at the distal end of the hollow tubular member, the cutting blade having an opening at an end thereof through which at least one of fluid, tissue or gaseous bubbles are aspirated when the surgical instrument is in use;
- at least one electrode disposed at the distal end of the hollow tubular member; and
- at least one aspiration hole, adjacent to the electrode, through a side of the hollow tubular member.

17. A surgical instrument as defined in claim 16, wherein the rotatable cutting blade is connected to a hollow drive shaft.

18. A surgical instrument as defined in claim 17, wherein the hollow drive shaft further includes at least one auxiliary hole through which bubbles can be aspirated.

19. A surgical instrument as defined in claim 16, wherein the electrode comprises at least a portion of an electronic surgical device that operates in at least one of a monopolar mode or a bipolar mode.

20. A method for aspirating gaseous bubbles at a surgical site, comprising:
- (a) providing a surgical instrument at the surgical site that provides both cutting and electrosurgical functions, the surgical instrument including a hollow member having a main opening through a distal end thereof;
- (b) ablating tissue at the surgical site using an ablation electrode at or near the distal end of the hollow member; and
- (c) aspirating gaseous bubbles generated in act (b) at the surgical site through at least one aspiration hole or slot disposed on a side of the hollow member adjacent to the ablation electrode and separate from the main opening of the hollow member.

* * * * *

UNITED STATES PATENT AND TRADEMARK OFFICE
CERTIFICATE OF CORRECTION

PATENT NO. : 6,610,059 B1 Page 1 of 1
DATED : August 26, 2003
INVENTOR(S) : Hugh S. West, Jr.

It is certified that error appears in the above-identified patent and that said Letters Patent is hereby corrected as shown below:

Column 8,
Line 52, change "assciated" to -- associated --

Column 11,
Line 23, change "ofthe" to -- of the --

Column 13,
Line 1, change "form" to -- from --

Signed and Sealed this

Ninth Day of December, 2003

JAMES E. ROGAN
*Director of the United States Patent and Trademark Office*